(12) United States Patent
Scheker et al.

(10) Patent No.: US 8,562,689 B2
(45) Date of Patent: *Oct. 22, 2013

(54) WRIST PROSTHESIS

(75) Inventors: Luis Roman Scheker, Glenview, KY (US); Bryan Babb, Jeffersonville, IN (US)

(73) Assignee: Aptis Medical, LLC, Glenview, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/355,222

(22) Filed: Jan. 20, 2012

(65) Prior Publication Data
US 2012/0136453 A1 May 31, 2012

Related U.S. Application Data (63) Continuation-in-part of application No. 12/098,034, filed on Apr. 4, 2008, now Pat. No. 8,333,806, which is a continuation of application No. PCT/US2006/039468, filed on Oct. 10, 2006, which is a continuation-in-part of application No. 11/306,311, filed on Dec. 22, 2005, now Pat. No. 8,052,757.

(60) Provisional application No. 60/726,113, filed on Oct. 13, 2005.

(51) Int. Cl.
*A61F 2/42* (2006.01)

(52) U.S. Cl.
USPC ..................... 623/21.13; 623/21.11

(58) Field of Classification Search
USPC .......... 623/21.11, 21.12, 21.13, 21.14, 21.15, 623/21.16, 21.17, 19.11, 19.12, 19.13, 623/19.14, 18.11, 20.11, 20.12, 20.13
See application file for complete search history.

(56) References Cited

U.S. PATENT DOCUMENTS

| | | | | |
|---|---|---|---|---|
| 5,458,646 | A * | 10/1995 | Giachino et al. | 623/21.12 |
| 5,951,604 | A * | 9/1999 | Scheker | 623/21.11 |
| 6,890,358 | B2 * | 5/2005 | Ball et al. | 623/21.13 |
| 8,052,757 | B1 * | 11/2011 | Scheker | 623/21.13 |
| 8,333,806 | B2 * | 12/2012 | Scheker | 623/21.13 |
| 2004/0225292 | A1 * | 11/2004 | Sasso et al. | 606/73 |
| 2009/0216334 | A1 * | 8/2009 | Leibel | 623/21.18 |

FOREIGN PATENT DOCUMENTS

FR 2875127 * 9/2004

* cited by examiner

*Primary Examiner* — David Isabella
*Assistant Examiner* — Marcia Hoffman
(74) *Attorney, Agent, or Firm* — Camoriano & Associates (57) ABSTRACT

A carpal plate for use in a wrist replacement prosthesis includes at least three non-linearly aligned, internally threaded openings, each opening defining a thread-screw axis with at least one thread-screw axis divergent from the other two thread-screw axes; and further including hollow core screws for the injection of a cement compound to aid in anchoring the screws into the cancellous portion of the carpal bones.

16 Claims, 12 Drawing Sheets

WRIST PROSTHESIS

This application is a continuation-in-part of U.S. application Ser. No. 12/098,034, filed Apr. 4, 2008, which is a continuation of PCT/US2006/039468 filed Oct. 10, 2006, which is a continuation-in-part of U.S. application Ser. No. 11/306,311, filed Dec. 22, 2005, which claims priority from U.S. Provisional Application Ser. No. 60/726,113 filed Oct. 13, 2005, all of which are hereby incorporated herein by reference.

BACKGROUND

The present invention relates to a wrist prosthesis. In particular, it relates to a wrist prosthesis with an improved mechanism for anchoring the prosthesis to the carpal bones of the wrist.

SUMMARY

One embodiment described herein uses offset, non-linearly-aligned, diverging hollow screws to secure the carpal plate of the wrist prosthesis to the carpal bones of the wrist. The hollow screws have cement ejection ports to allow for the injection of cement through the interior of the hollow screw and into the area immediately adjacent the threads of the screw. The screws are threaded into the cancellous bone (the softer, less compact, less dense portion of the bone), and the injection of the cement adjacent the screw threads both helps anchor the screws immediately and then further improves the securement of the screws to the carpal bones as it causes the body to grow cortical bone (the harder, more compact, denser type of bone) in the area surrounding the screw threads.

DESCRIPTION

FIGS. 1-3F show one embodiment of a wrist prosthesis 10 made in accordance with the present invention. The wrist prosthesis 10 includes a radial brace member 12, which is secured to the radius bone 22 with a plurality of screws 14. Also included is an ulnar brace member 16, which is secured to the ulna bone 24, typically via a press fit into the medullary cavity 48 of the ulna 24. In addition to (or instead of) the press fit, the brace member 16 may be cemented, adhered, or secured by other means to the ulna 24.

Figure 3:
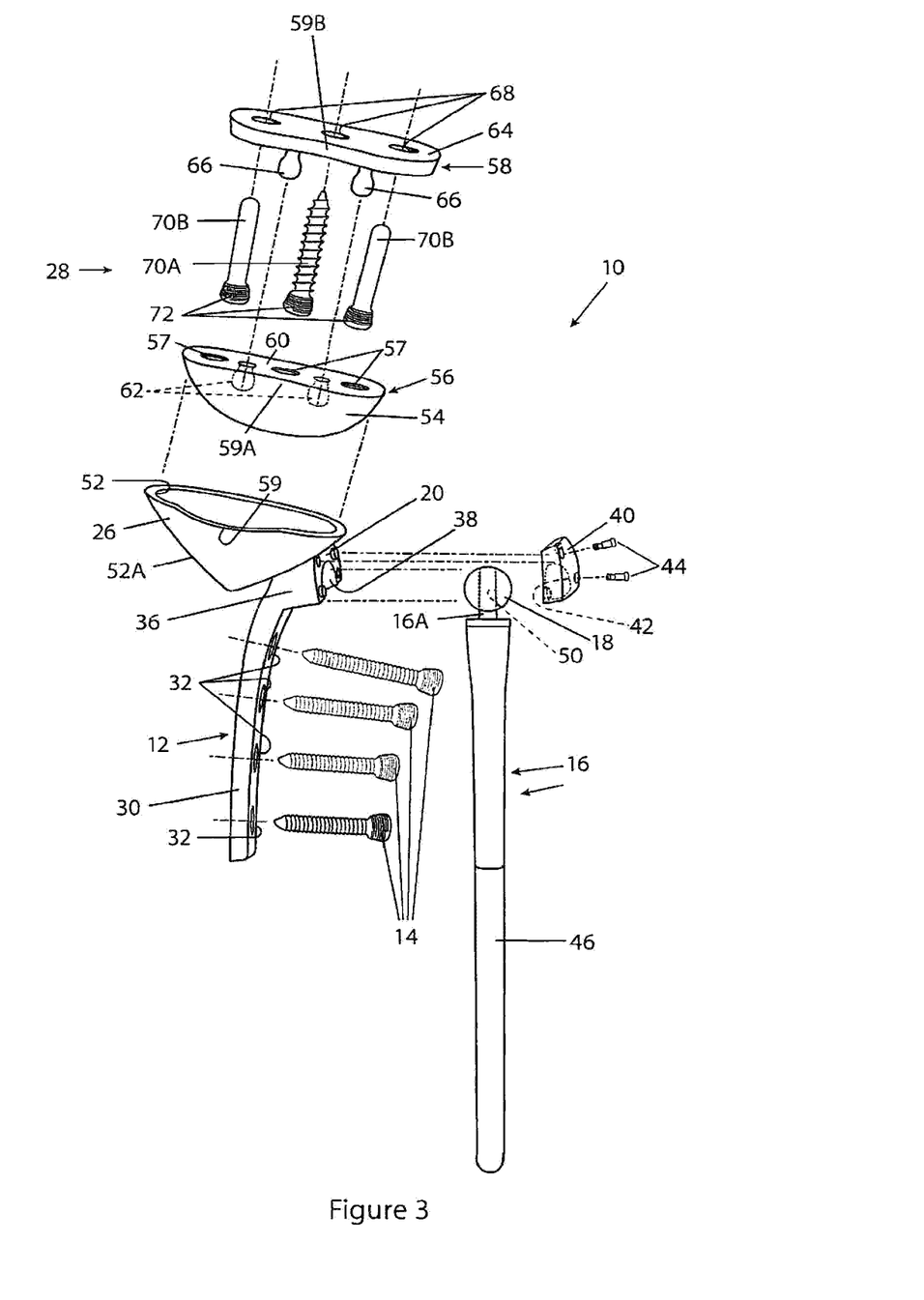
FIG. 3 is an exploded perspective view of the wrist prosthesis of FIG. 1.

The ulnar brace member 16 is essentially a shaft, symmetrical about a central axis. A spherical ball 18 is mounted onto the shaft 16 at one end. The ball 18 has a bore 50 along its diameter which receives a reduced cross-section end portion 16A of the shaft 16. The ball 18 is free to pivot about the axis of the shaft 16 and to translate axially along the end portion 16A of the shaft 16.

Looking in more detail at the ulnar brace member 16, it includes an elongated ulnar stem rod 46, which is inserted into the medullary cavity 48 (See FIG. 2) of the ulna 24. The ulnar stem rod 46 may be press fit or may be cemented into this medullary cavity 48. In this embodiment, a portion of the ulnar stem rod 46 is coated to provide a porous surface, into which the bone will grow to help secure the rod 46 in position. The reduced diameter distal end 16A of the ulnar stem rod 46 is received in a bore 50 through the diameter of the ball 18 so as to permit translational movement of the ulnar stem rod 46 relative to the ball 18 along the axis of the ulnar brace member 16.

As shown best in FIG. 3, the radial brace member 12 includes a base portion 20, which defines a partial spherical cavity 38. The cover 40 also defines a partial spherical cavity 42. When the cover 40 is secured to the base 20 by means of screws 44, the spherical ball 18 of the ulnar brace member 16 is trapped in the partial spherical cavity formed by the base portion 20 and cover 40 and is free to swivel within and bear against the surface of that cavity, in order to support the radius 22 relative to the ulna 24 for pronation and supination of the forearm and for the bearing of weight. The bearing surface 38 is nearly in the position of the sigmoid notch of the original radius, and the ball 18 is nearly in the position of the ulna head of the original ulna, so the joint provides the same relative positions of the radius and ulna throughout the entire pronation and supination of the forearm as would have been provided by the original intact joint. This means both that the axes of the radius 22 and ulna 24 are in the same relative positions and that the longitudinal position of the joint along the axes of both bones is in the same relative position as it would have been in the original joint.

In this particular embodiment, the bearing surface 38 is 1-2 millimeters in the ulnar direction from the original bearing surface that was provided by the cartilage in the sigmoid notch of the original joint, and the ball 18 has a radius that is 1-2 millimeters smaller than the original ulna head, so, while the actual bearing surface is offset 1-2 millimeters in the ulnar direction from the bearing surface of the original intact joint, the relative positions of the bones are the same as in the original intact joint. Obviously, there will be some tolerances involved in the actual production and installation, but it is preferred that the relative positions of the bones be within two millimeters of their original intact positions.

Figure 1:
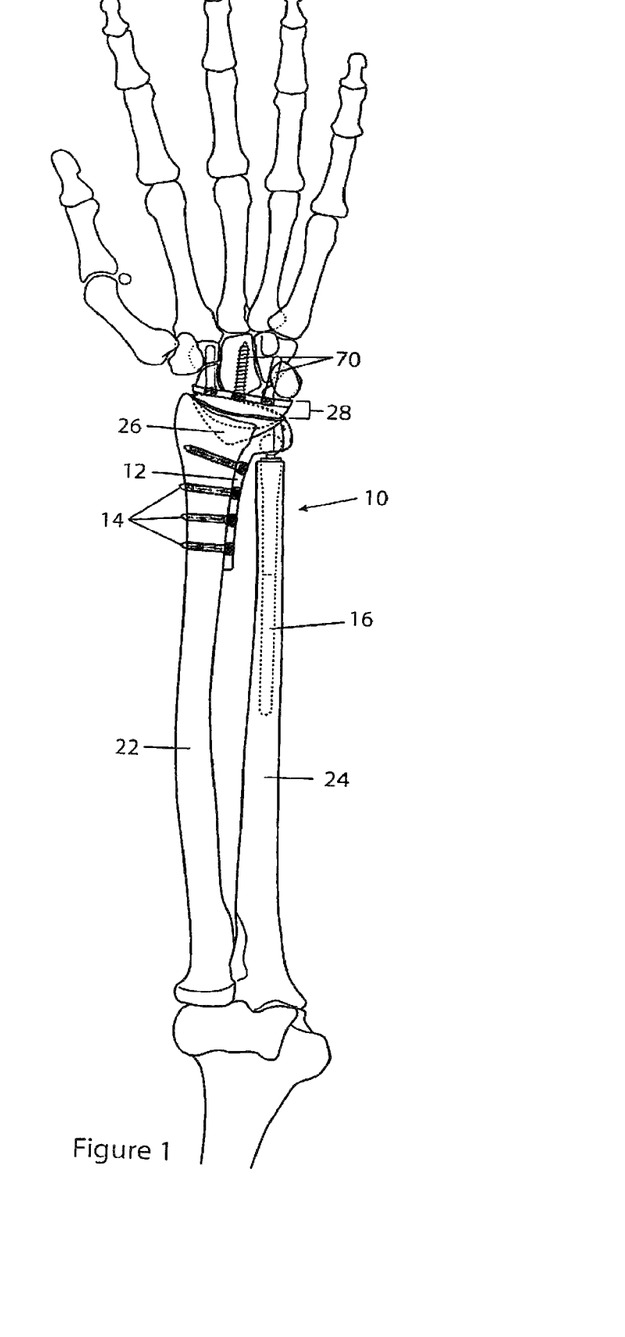
FIG. 1 is a front view of one embodiment of a wrist prosthesis installed on a human skeleton.
Figure 2:
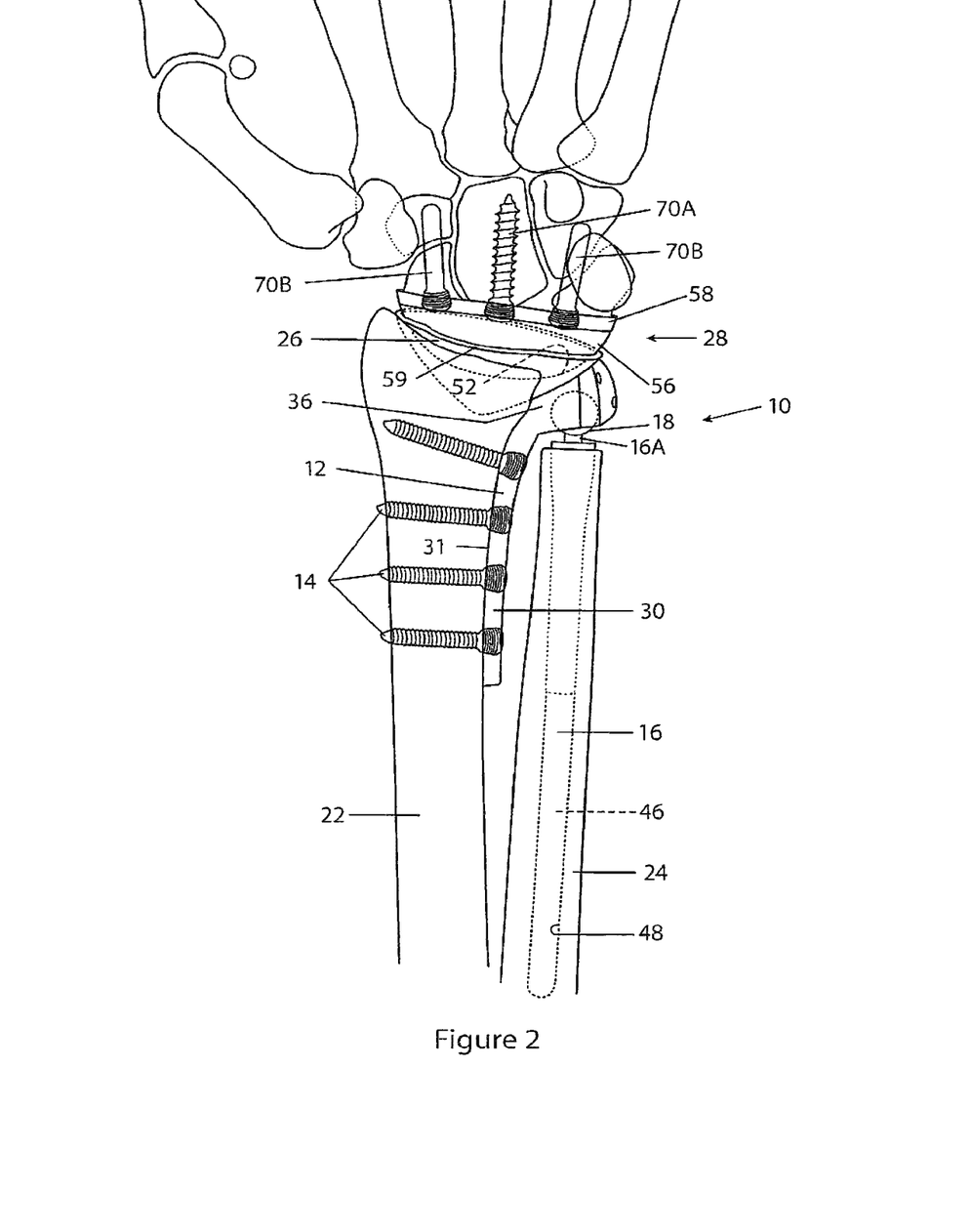
FIG. 2 is an enlarged view of the installed wrist prosthesis of FIG. 1.

Referring to FIGS. 2 and 3, the radial brace member 12 includes an elongated portion 30, which lies adjacent to the outer surface of the radius bone 22 and is secured to the radius 22 by means of screws 14 that extend through threaded openings 32 in the elongated portion 30. A radius abutment surface 31 of the elongated portion 30 conforms to the outer surface of the side of the radius bone 22 that faces the ulna 24, providing a large contact surface between the brace member 12 and the radius bone 22. The particular screws 14 shown here have two different sets of threads. The thread along the shank is threaded into the bone, and the thread along the head is threaded into the respective threaded opening 32. Of course, other types of fasteners could be used instead of or in addition to these screws 14.

As indicated above, the ball 18 also is able to rotate within the partial spherical cavity formed by the base 20 and the base cover 40. This arrangement provides support of the radius 22 relative to the ulna 24 through the full range of motion from pronation to supination of the hand. The cover 40 ensures that the ball 18 of the ulnar brace 16 will remain engaged with the radial brace 12 so it can bear against the bearing surface 38 to provide the desired support. The cover 40 essentially replaces the function of the ligaments that originally held the radius in position relative to the ulna head. The portion of the prosthesis 10 described thus far is very similar to a distal radioulnar joint replacement prosthesis described in U.S. Pat. No. 5,951,604 "Scheker", which is hereby incorporated herein by reference.

The wrist prosthesis 10 further includes a concave articular socket 26, which is fixed relative to the radial brace member 12, and a convex articular member 28, which is fixed relative to the patient's hand and which fits into and slides relative to the articular socket 26.

In this embodiment, the articular socket 26 is an integral part of the radial brace member 12. Alternatively, the articular socket 26 could be a separate piece which is fixed to the radial brace member 12 by such means as welding, bolting, snapping together, or any other suitable means.

The articular socket 26 defines a concave ellipsoidal surface 52 (which may also be referred to as a reverse-ellipsoidal surface), which receives the mating convex ellipsoidal surface 54 of the articular member 28 as described in more detail below. Since the articular socket 26 is fixed relative to the radial brace member 12, it is supported by and secured to the radius 22 as well as being supported by the ulna 24 through the ball joint. As best shown in FIG. 2, the concave ellipsoidal surface 52 extends laterally in the direction of the ulna 24 to a point beyond the center of the cavity formed by the partial spherical cavities 38, 42 of the base 20 and base plate 40, and beyond the center of the spherical ball 18, which means that it extends beyond the axis of the ulna 24 (and beyond the axis of the ulnar brace 16, with is coaxial with the ulna 24). It also extends in the ulnar direction beyond the bearing surface of the cavity 38, which is in the position of the original sigmoid notch. This allows the articular socket 26 to provide a wider bearing surface than is present in the natural human wrist.

In this embodiment, the articular socket 26 forms a cup with a generally uniform wall thickness, so it also defines a convex outer surface 52A opposite the concave ellipsoidal surface 52 (see FIG. 3). The outer surface 52A of the articular socket 26 generally conforms to the natural recess at the distal end of the radius bone 22, thereby minimizing the amount of the bone that is removed to accommodate the socket 26. Usually, only a small amount of bone matter is removed toward the center of the radius bone 22 to receive the socket 26, thereby leaving the length of the radius bone unchanged. This is different from the mounting arrangements of the prior art, in which the end of the radius bone 22 typically is cut off flat, thus reducing the length of the bone. There typically is damage to the bone that gives rise to the need for an artificial joint, so the preparation required to mount the radial brace 12 on the radius 22 will vary in each case. However, in a typical case, a small amount of bone matter is removed toward the center of the radius 22 at its distal end to receive the socket 26, and any cartilage (if present) is removed from the ulnar side of the radius 22 at the sigmoid notch, so the radial brace 12 can fit snugly against the radius 22. This leaves the radius 22 at its full length.

In this embodiment, the articular member 28 includes an articular base member 56 and a distal plate 58.

The articular base member 56 defines the convex ellipsoidal surface 54, which mates with and slidably engages the concave ellipsoidal surface 52 of the articular socket 26 for movement of the base 56 relative to the articular socket 26. The top surface 60 of the articular base member 56 is substantially flat and defines three round indentations 57. The flat top surface 60 also defines two tear-shaped cavities 62 for the attachment of the distal plate 58 to the articular base member 56, as described below.

The distal plate 58 (also referred to as a carpal plate 58) is a substantially flat member 64, with two downwardly-extending tear-shaped projections 66. These projections 66 are sized to snap-fit into the corresponding tear-shaped cavities 62 in the base 56 in order to secure the distal plate 58 to the base 56. The distal plate 58 further defines three threaded through openings 68 to accommodate elongated fasteners 70A, 70B, which secure the distal plate 58 to the carpal bones of the hand. (The fasteners could extend into the metacarpals if desired.) The fasteners in this embodiment are a screw 70A and two pegs 70B, as shown in FIG. 3. Each of these fasteners 70A, 70B includes a threaded portion 72 at the head end, which includes self-locking threads that are threaded and locked into the corresponding threaded surface in the respective opening 68 of the distal plate 58. The articular base member 56 includes three round indentations 57 for receiving the heads of the fasteners 70A, 70B.

In this embodiment, the articular socket 26 of the radial brace member 12, as well as the base 56 and distal plate 58 of the articular member 28, further define curved, recessed surface portions 59, 59A, and 59B, respectively, in the front, or volar, side of the prosthesis 10, to provide a guiding surface for guiding the median nerve and flexor tendons 61 over the wrist. This arrangement can be seen best in FIGS. 3E and 3F. While these recessed surface portions are not required, it is preferred that at least the recessed surface portion 59 of the articular socket 26 be provided to help guide and ease the transition of the median nerve and flexor tendons 61 over the wrist.

To help define the orientation of the various parts of the wrist and the components of the wrist prosthesis 10, it should be noted that there is an ulnar side (laterally in the direction of the ulna bone), a radial side (laterally in the direction of the radius bone), a front or volar side (toward the palm), and a back or dorsal side (toward the back of the hand).

In this embodiment, the ellipsoidal surface 52 of the articular socket 26 is wider in the radial-ulnar direction than the volar-dorsal direction, and the radius of curvature in the radial-ulnar direction is greater than the radius of curvature in the volar-dorsal direction. The recesses 59, 59A, 59B are formed in the front, or volar, side of the prosthesis 10, so they essentially replace the proximal portion of the carpal tunnel of the wrist, providing the guiding surface that receives the median nerve and flexor tendons 61 in the wrist as best shown in FIGS. 3E and 3F, which helps reduce wear on the nerve and tendons.

Figure 3A:
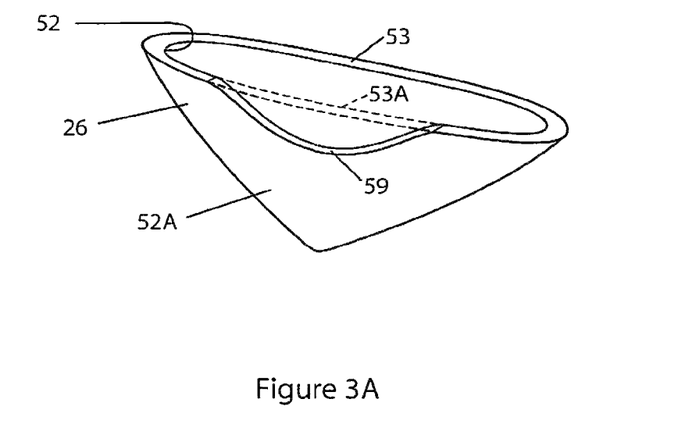
FIG. 3A is a perspective view of the articular socket of the wrist prosthesis of FIG. 1.

FIG. 3A is a detailed view of the articular socket portion 26 of the radial brace member 12, showing that the recess 59 extends from the distal edge 53 of the articular socket 26 towards the proximal end of the articular socket 26 to define a centrally recessed guide surface. The phantom lines 53A in FIG. 3A show what the edge 53 would look like if it were entirely planar, without the central recess 59. As best seen in FIG. 2, the recess 59 is formed on the front, or volar, side of the prosthesis 10 in the location of the carpel tunnel of the natural wrist.

Figure 3B:
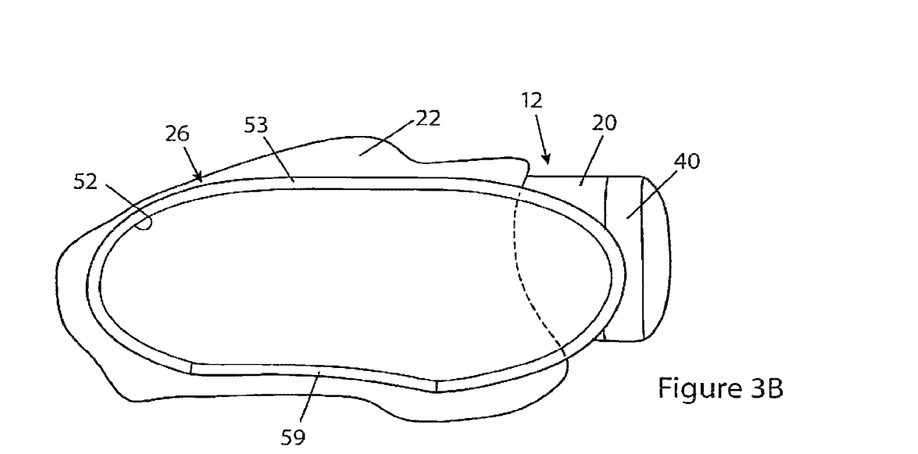
FIG. 3B is a distal end view looking down on the articular socket portion of the wrist prosthesis of FIG. 1.
Figure 3C:
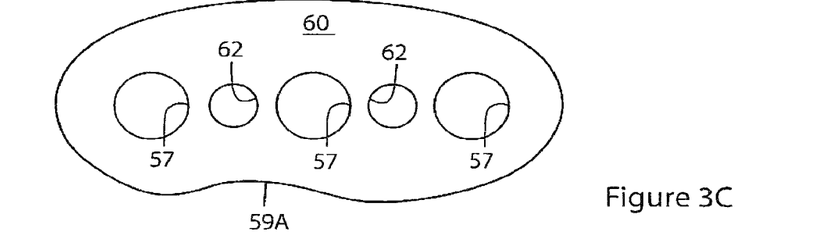
FIG. 3C is a plan view of the articular base member of the wrist prosthesis of FIG. 1.
Figure 3D:
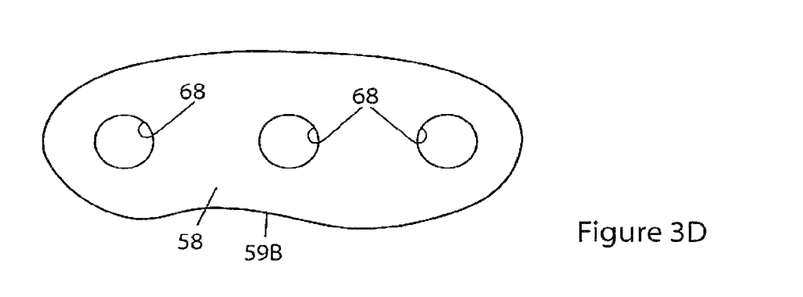
FIG. 3D is a plan view of the distal plate of the wrist prosthesis of FIG. 1.
Figure 3E:
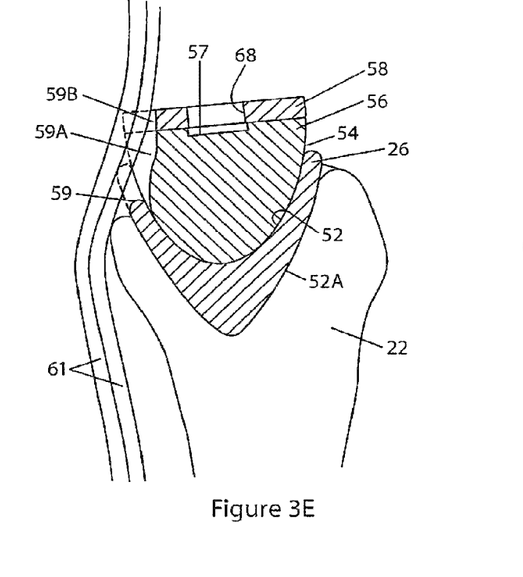
FIG. 3E is a schematic sectional view of the articular socket and articular member of the wrist prosthesis of FIG. 1.
Figure 3F:
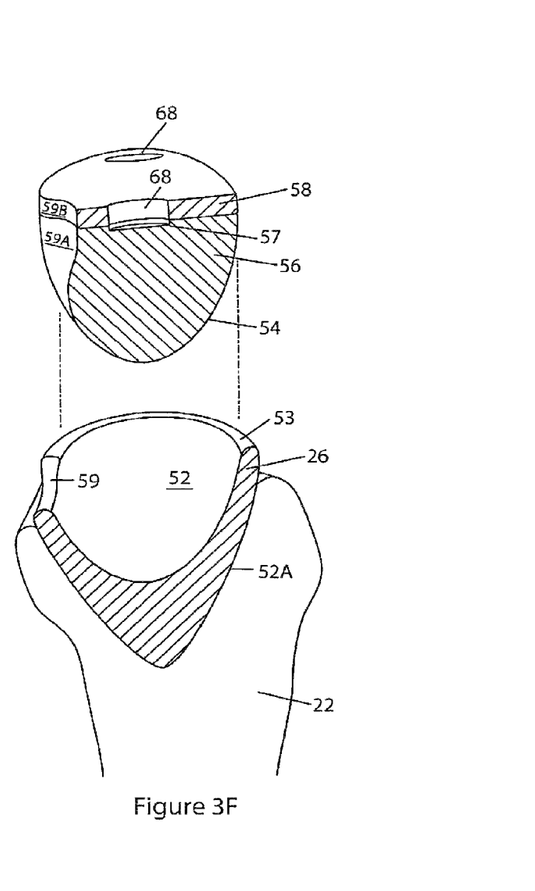
FIG. 3F is a schematic exploded perspective sectional view of the articular socket and articular member of the wrist prosthesis of FIG. 1.

FIG. 3B is a distal end view of the radial brace member 12 and radius bone 22, looking down on the articular socket 26. In this view it can be seen that the curved central recess 59 in the articular socket 26 is on the volar side and curves both downwardly, toward the proximal end of the socket 26, and inwardly, toward the dorsal side of the socket 26. FIGS. 3C and 3D are distal end views of the articular base member 56 and the distal plate 58, respectively, showing the indentations 57 and tear-shaped cavities 62 in the articular base member 56 and the threaded openings 68 in the distal plate 58. The articular base member 56 has a curved central recess 59A on the volar side, and the distal plate 58 also has a curved central recess 59B on the volar side. As was explained above, the curved central recesses 59, 59A, 59B are aligned to provide a guide surface that essentially replaces the proximal portion of the carpal tunnel of the natural wrist.

When the articular base member 56 and distal plate 58 are fitted together, with the tear-shaped projections 66 snapped into the tear-shaped recesses 62, to form the articular member 28, the recesses 59A, 59B are aligned with each other. Once the articular member 28 and articular socket 26 are mated together, the recesses 59, 59A, 59B align with each other, providing a guide surface similar to the carpel tunnel of the wrist and guiding the median nerve and flexor tendons. By providing a gradual, guided transition over the wrist, the recesses 59, 59A, 59B reduce wear on the nerve and tendons of the wrist.

FIG. 3B also shows that the ellipsoidal surface 52 of the articular socket 26 is wider in the radial-ulnar direction than the volar-dorsal direction, and it extends across the full width of the wrist in order to provide a large supporting surface area. The ellipsoidal surface 52 extends from a point outside of (or beyond) the longitudinal axis of the radius 22 in the radial direction to a point beyond the axis of the radial brace 12 in the ulnar direction, projecting over a portion of the cover 40, and over both the radial-most and the ulnar-most points on the ball 18 (i.e. the point farthest in the radial direction and the point farthest in the ulnar direction, as shown in FIG. 2). FIG. 3B also shows that the base 20 of the radial brace member 12 is on the ulnar side of the articular socket 26.

In this particular embodiment, the metal components of the prosthesis 10 are made from cobalt chromium. These metal components include the radial and ulnar brace members 12, 16, the cover 40, the securing screws 14, 44, 70A, and pegs 70B, the articular socket 26, and the distal plate 58, including its two tear-shaped projections 66. The non-metal components are made from an ultra-high molecular weight polymer, such as UHMW polyethylene. These non-metal components include the ball 18 and the base 56 of the articular member 28.

To assemble and install the wrist prosthesis 10, first the distal radioulnar joint is installed as described in the aforementioned U.S. Pat. No. 5,951,604 "Scheker", with the only change being that some of the distal end of the radius probably will need to be removed as described earlier in order to receive the articular socket 26. At this point, the radial brace member 12 is secured into the radius 22, the ulnar brace member 16 is secured onto the ulna 24, and the ball 18 is secured in the recess formed between the cover 40 and the base 20 to form a ball joint.

Next, the proximal ends of the carpal bones are excised to fit flat against the distal plate 58 of the articular member 28. With the wrist bent downwardly, holes are drilled in the carpal bones as required (and preferably with the aid of a template) to receive the fasteners 70A, 70B. Then, the fasteners 70A, 70B are extended through the openings 68 in the distal plate 58 and into the holes that have been drilled in the carpal bones, and the fasteners 70A, 70B are rotated to thread them into the threaded openings 68 in the distal plate 58. The head end of the fasteners 70A, 70B has a recess (not shown) that allows a rotational driver such as a screwdriver or Allen wrench to rotationally drive the fasteners. The screw 70A also is threaded into the hole that has been drilled in its respective carpal bone, thereby securing the distal plate 58 to the carpal bones. The screw 70A prevents the distal plate 58 from pulling away from the carpal bones, and the pins 70B prevent the distal plate 58 from rotating or sliding relative to the carpal bones. The pins 70B also prevent the distal plate 58 from pulling away from the carpal bones, because they are inserted at an angle, creating a wedge effect. While one screw 70A and two pegs 70B are shown, any combination of screws and pegs may be used, as well as other fastening means for securing the distal plate 58 to the carpal bones of the wrist. It may be desirable to provide a porous surface on the pegs 70B or other fasteners into which the bone may grow to provide an even more secure attachment.

The wrist is then pushed back up, being careful to align the tear-shaped projections 66 in the distal plate 58 with the tear-shaped cavities 62 in the base 56, and the distal plate 58 and base 56 are pushed together until the tear-shaped projections 66 in the distal plate 58 snap into the tear-shaped cavities 62 in the base 56. The base 56 is then inserted into the cavity 52 of the articular socket 26 to complete the assembly. The existing tendons and ligaments of the wrist help retain the articular member 28 in the articular socket 26 at the distal radius.

This arrangement allows a full range of motion, as well as providing support of the wrist joint by both the radius 22 and the ulna 24. It also should be noted that the distal plate 58 and the corresponding ellipsoidal surfaces of the articular member 28 and the articular socket 26 extend across the full width of the wrist in order to provide a large supporting surface area as the articular member 28 slides within the articular socket 26. The prosthesis is also well-supported by both the radius 22 and the ulna 24, which permits the wrist joint to support a substantial amount of weight or loading without causing pain and without damaging the joint, while permitting a full range of motion that closely mirrors the range of motion of the natural wrist joint.

Figure 4:
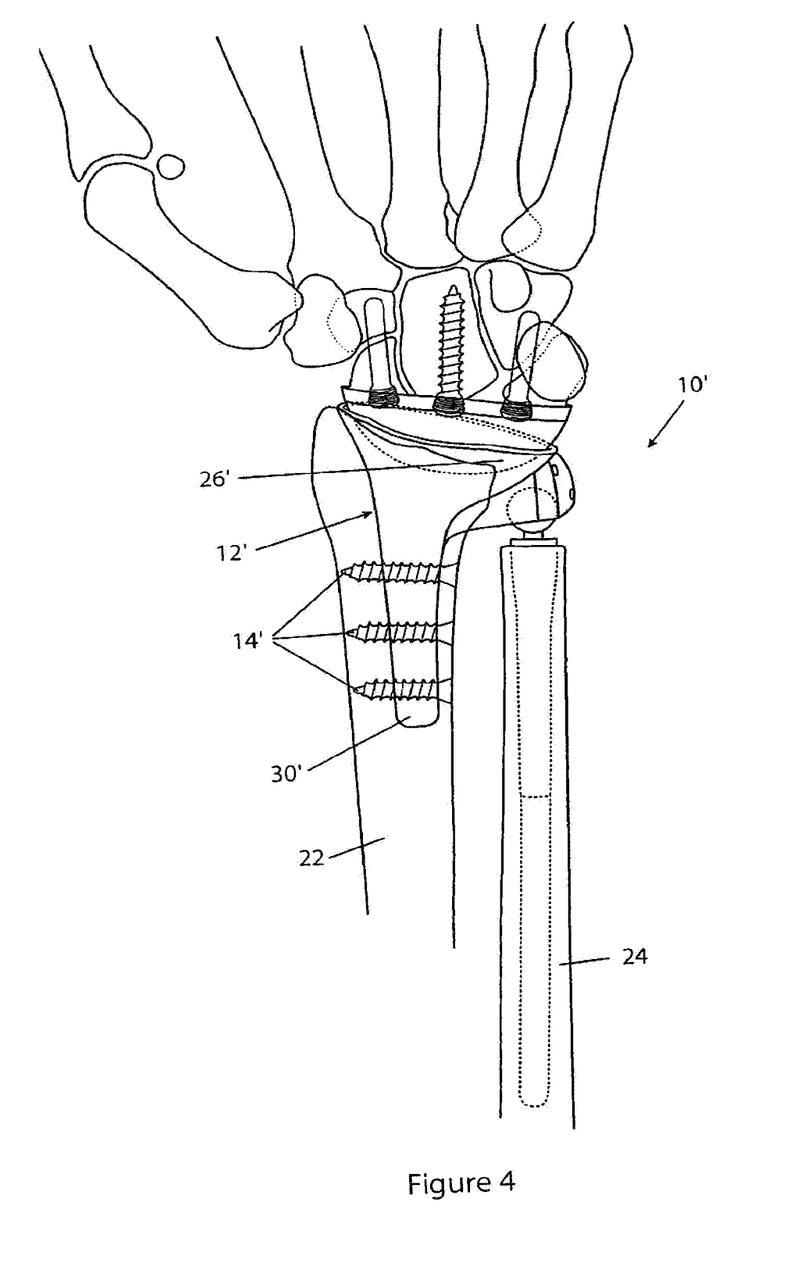
FIG. 4 is a view similar to FIG. 2, but for a second embodiment of an installed wrist prosthesis made in accordance with the present invention.
Figure 5:
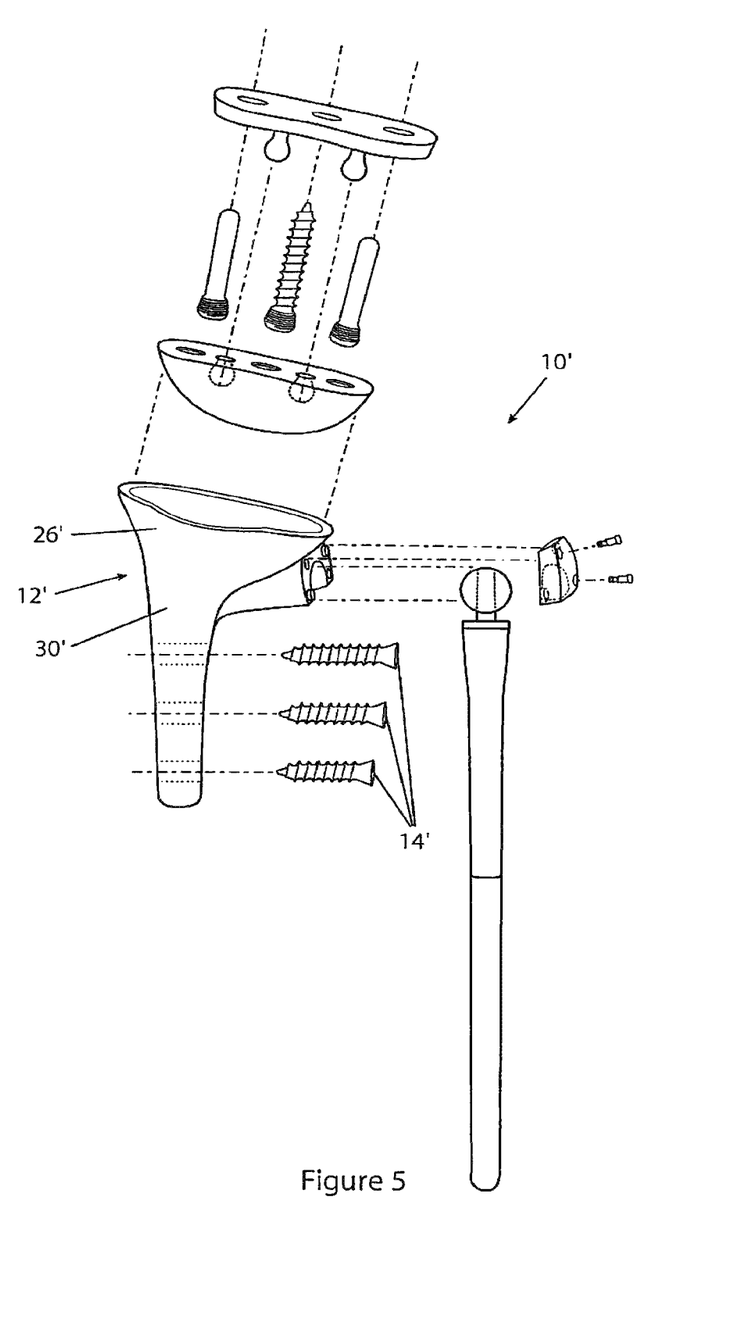
FIG. 5 is an exploded perspective view of the wrist prosthesis of FIG. 4.

FIGS. 4 and 5 show a second embodiment of a total wrist replacement prosthesis 10' made in accordance with the present invention. This embodiment 10' is very similar to the first embodiment 10 described above, except that the location and installation of the radial brace member 12' is different. In this embodiment, the radial brace member 12' is inserted into the medullary cavity of the radius 22, and may make use of cement or other methods of attachment such as screws 14'. All the other components of this embodiment 10' and its method of operation remain substantially the same as in the first embodiment 10. This embodiment provides a larger contact surface area between the articular socket 26' and the elongated portion 30' of the radial brace member 12', which may result in greater structural integrity of the prosthesis 10'. Of course, in this embodiment, more of the central portion of the radius bone 22 would have to be removed in order to mount the radial brace member 12'. However, the full length of the radius bone 22 is still preserved. At this point, the first embodiment of the prosthesis 10 is preferred, as it appears that mounting to the outside of the radius bone 22 provides greater structural support for the prosthesis.

Figure 6:
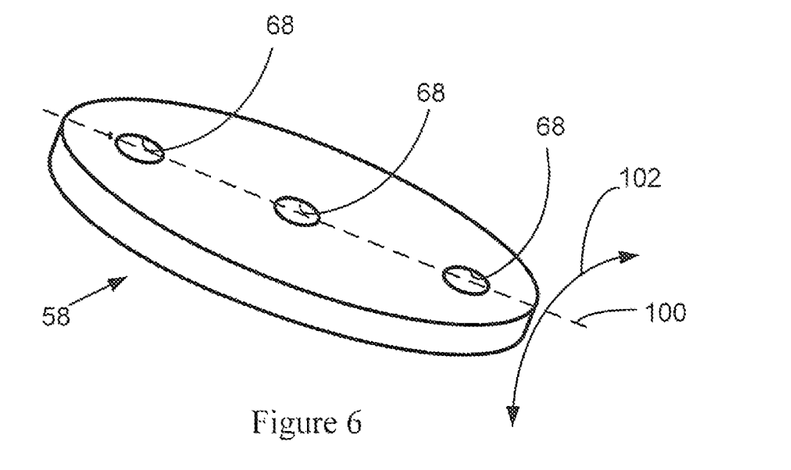
FIG. 6 is a schematic perspective view of the carpal plate of FIG. 3D, showing the openings for the attachment screws substantially linearly aligned.

FIG. 6 is a perspective view of the carpal plate 58 of FIG. 3D, with the openings 68 all linearly-aligned along the axis 100. The points of the central axes of the three aligned openings 68 located at the top surface of the carpal plate 58 define a line (the major axis 100 of the elliptical plate 58). Since those points define a line, it is possible that the carpal plate 58 may be able to rock about that line relative to the carpal bones, as shown by the arrow 102, which is not desirable.

Figure 7:
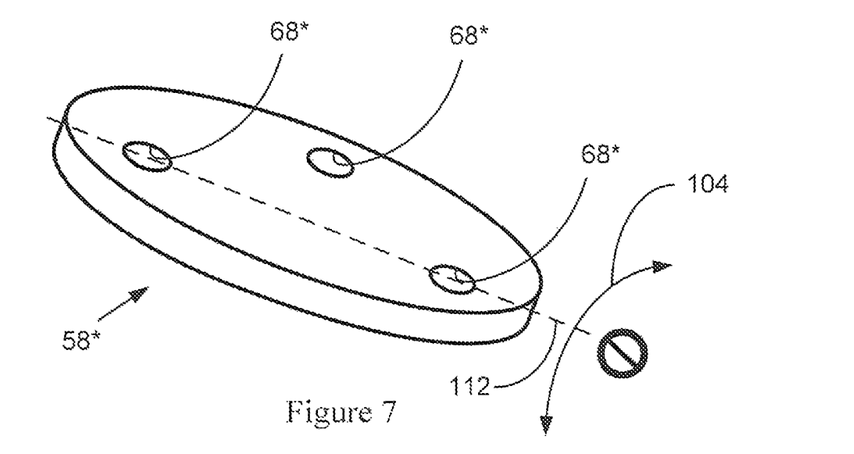
FIG. 7 is a schematic perspective view of an alternative carpal plate wherein the openings for the attachment screws are not linearly aligned with each other but instead are offset from each other.

FIG. 7 is a perspective view of a carpal plate 58*, similar to the carpal plate 58 of FIG. 6, but with the three internally-threaded openings 68* being offset from (not linearly-aligned with) each other. (The tear-shaped projections 66 extending downwardly from the bottom surface of the plate 58* are not seen in this view but are identical to the tear-shaped projections 66 of the plate 56 shown in FIG. 3.) Because the openings 68* are non-linearly arranged, the three points defined by their longitudinal axes at the top surface of the carpal plate 58* define a plane, not just a line. This makes this mounting arrangement more stable than the arrangement of FIG. 6, so that, when a turning moment is applied to the plate 58*, as shown schematically by the double-ended arrow 104, this mounting arrangement resists a pivoting motion about any axis.

It should be noted that both the shank 122 and the head 120 of each screw 108 is threaded. The enlarged head 120 is threaded to engage the internal threads in the openings 68* of the carpal plate 58*, while the shank has deeper and more aggressive threads to engage the respective carpal bone into which it is threaded.

To provide a more secure attachment of the screws holding the carpal plate 58* to the carpal bones, the openings 68* are drilled and internally tapped to define a thread-screw axis at an angle α (See FIG. 9) to the plane defined at the top surface of the carpal plate 58* as described above. The angle α for each thread-screw axis is preferably between 70 degrees and 85 degrees, and the angles preferably are such that all three thread-screw axes diverge from each other, with no thread-screw axis being parallel to any other thread-screw axis. It is also preferable that at least one of the three thread-screw axes is not coplanar with the other two, and most preferable that no two of the thread-screw axes are coplanar. It should be noted that the angle α need not necessarily be the same for all three screws 108. For instance, the angle α may be a more aggressive angle, such as 70 degrees, for one or two of the screws and a less aggressive angle, such as 85 degrees, for the third screw.

Referring again to FIGS. 7 and 9, each of the internally tapped openings 68* in the carpal plate defines a thread-screw axis that is fixed relative to the carpal plate 58* prior to inserting screws 108 through the openings, so that the carpal plate defines fixed angles for the screws 108 as the screws 108 are being inserted, to ensure that the longitudinal axes of the screws 108 diverge from each other, with each longitudinal axis extending at a desired angle α.

Figure 10:
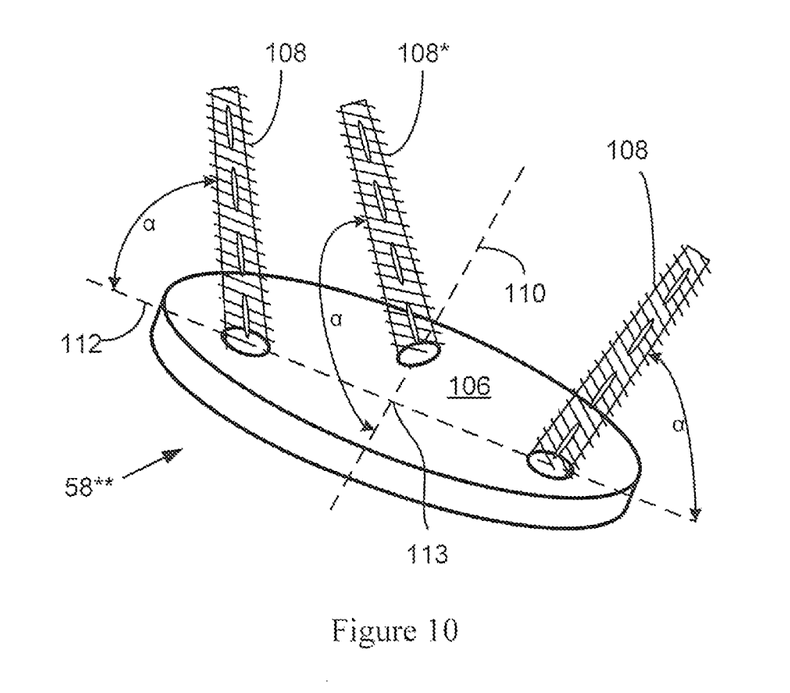
FIG. 10 is schematic perspective view of another embodiment of a carpal plate similar to the plate of FIG. 9, but with the holes oriented differently in order to cause the attachment screws to extend in a slightly different orientation.

FIG. 10 shows another embodiment of a carpal plate 58 which shows that the angle α of the longitudinal axis of the screws 108 need not necessarily be in a direction diverging away from the center point 113 of the plate 58 for all the screws 108. In this embodiment, the screws 108 at the longitudinal ends are angled outwardly, away from the center point 113, while the third screw 108* is angled inwardly, toward the center point 113. As long as the axes of the screws 108 diverge from each other, and are not parallel to each other, they make it difficult for the plate 58* or 58** to be removed from the carpal bones into which the screws extend.

Figure 9:
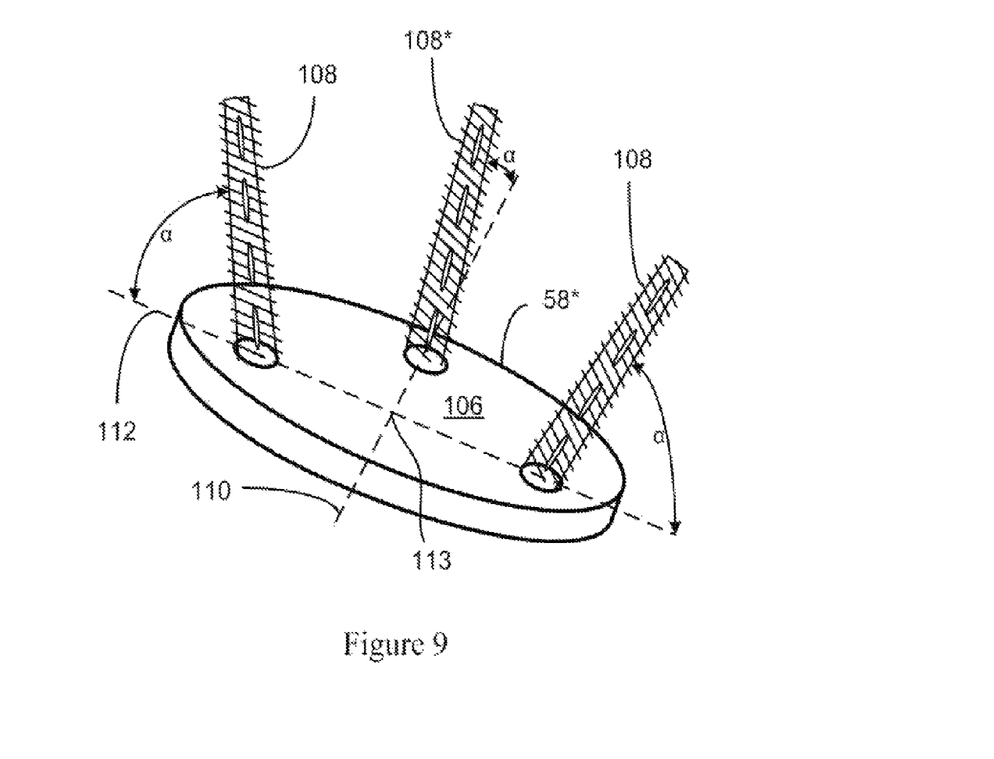
FIG. 9 is a schematic perspective view of the carpal plate of FIG. 7 with the attachment screws of FIG. 8.
Figure 12:
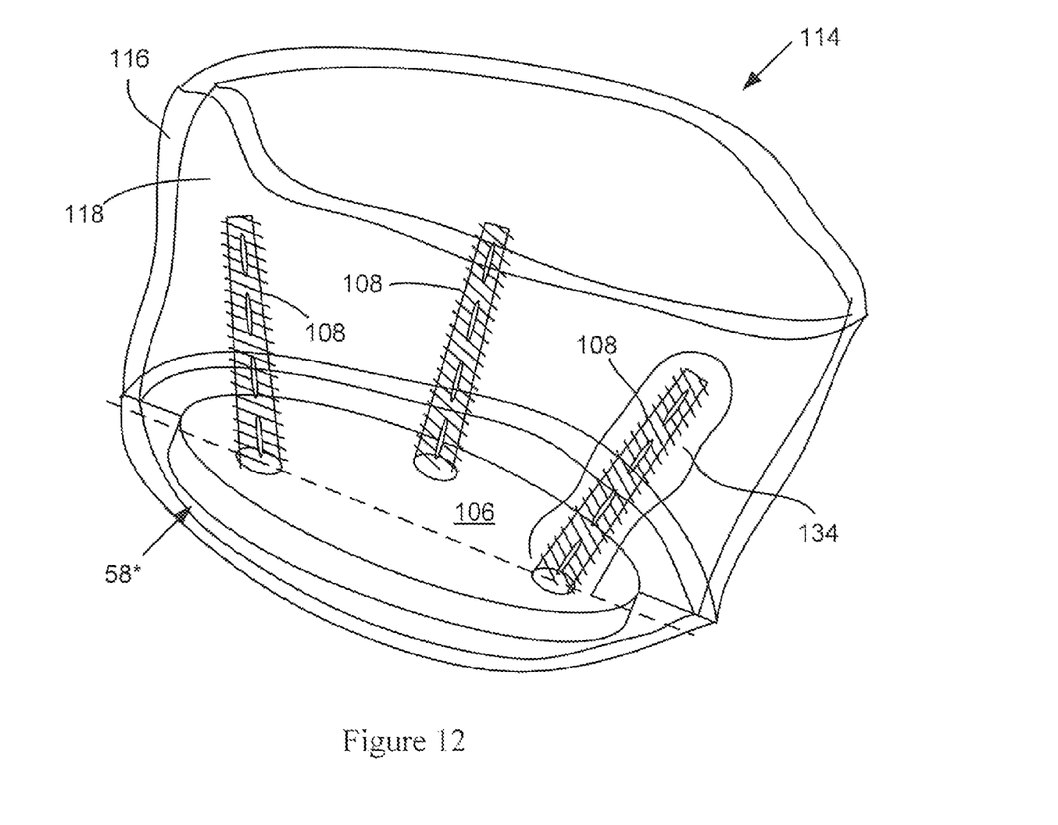
FIG. 12 is a schematic perspective view of the carpal plate of FIG. 9 installed on a broken away portion of a carpal bone and showing the injection of cement into the cancellous bone from one of the attachment screws.

FIG. 12 is a partially broken-away, schematic view of the carpal plate 58* of FIG. 9 installed on a schematic bone 114 which represents the carpal bones of the wrist. The bone 114 includes a cortical bone portion 116 which is a harder, more compact, denser portion of the bone 114, and which envelops a cancellous bone portion 118 which is a softer, less compact, less dense portion of the bone 114.

The screws 108 extend into the softer, cancellous bone portion 118. The fact that the screws 108 extend in diverging directions helps ensure that they will not pull loose. In addition, to further improve the hold of the screws 108, a biological bone cement 134 may be injected through the screws 108 and into the area surrounding the threads of the screws 108, as shown in FIG. 12 and as explained in more detail below.

Figure 8:
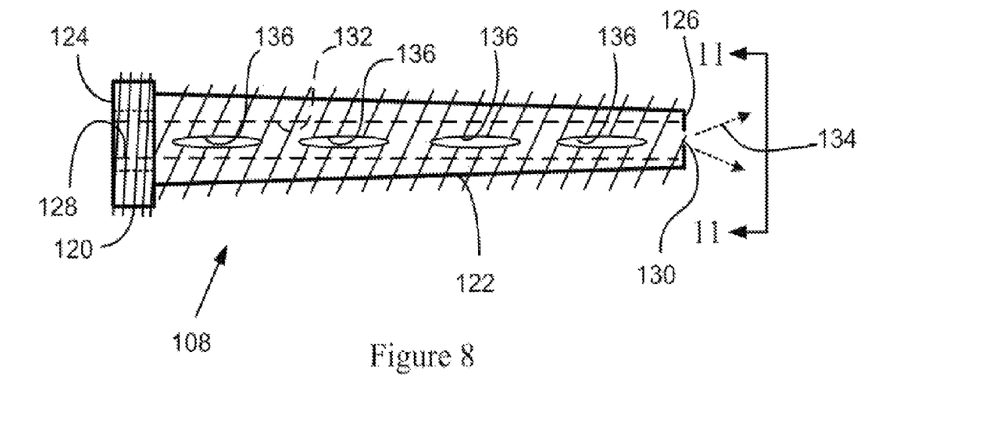
FIG. 8 is a schematic side view of an attachment screw for use with the carpal plate of FIG. 7.
Figure 11:
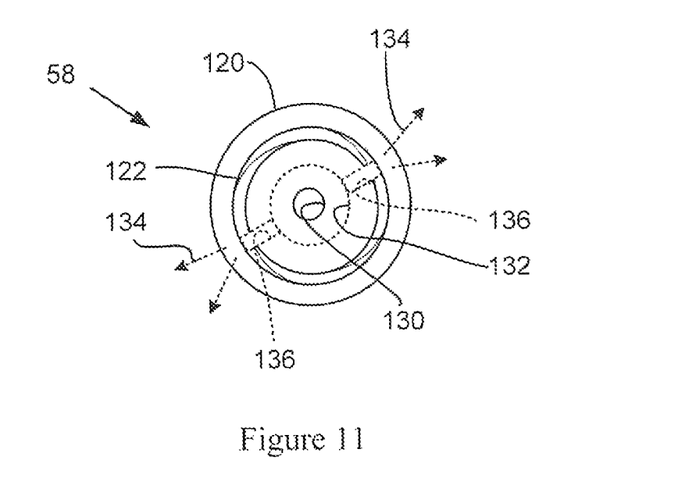
FIG. 11 is a view along line 11-11 of FIG. 8.

Referring to FIGS. 8, 11 and 12, each of the screws 108 is hollow along its axis and includes a threaded head portion 120 and a threaded shank portion 122. The threaded head portion 120 has a larger diameter than the threaded shank portion 122. The elongated hollow center of the screw 108 is open at both ends 124, 126, with the opening 128 at the head portion 120 having a larger diameter to facilitate injecting a biological bone cement 134 into and through the interior cavity 132 of the screw 108. The opening 130 at the second end 126 has a smaller diameter.

The threaded shank portion 122 of the screw 108 defines a plurality of longitudinally aligned slotted openings 136 which extend into the elongated hollow central cavity 132 providing passageways for the biological bone cement 134 to flow from the opening 128 at the head end, through the hollow central cavity 132, and out the slotted openings 136 into the area 134 (See FIG. 12) surrounding the threaded shank portion 122 of the screw 108.

FIG. 11 is an end view of the screw 108 as seen from the end opposite the head portion 120 and shows the biological bone cement 134 being ejected from the screw 108 via the openings 136. Of course, the openings 136 need not be symmetrically located along the threaded shank portion 122 of the screw 108. In FIG. 11 the openings 136 are shown to be diametrically opposed to each other, 180 degrees apart. There may be any number of openings 136, arranged as desired to achieve the best flow of bone cement into the carpal bone surrounding the screw 108.

Once the carpal plate 58* has been secured to the carpal bones of the wrist, as shown in FIG. 12, a biological bone cement 134 is injected through the head portion 120 of each screw 108, into the cavity 132 and out through the side openings 136 and the end opening 130 so as to flow into the cancellous bone portion 118 adjacent the threaded portion 122 of each screw 108, as shown in the rightmost screw 108 in FIG. 12. The biological bone cement 134 not only provides an immediate purchase for the screws 108 onto the cancellous bone portion 118 of the bone 114; it also promotes cortical bone growth around the threaded portion 122 of the screws

108. Once the stronger, cortical bone has grown into this area, it provides even better anchoring of the screws 108 and therefore better anchoring of the carpal plate 58\* for the long term.

Of course, the articular base member 56 that mates with the plate 58\* or **58\*\* will be modified to have recesses 57 that are properly aligned with the openings 68\*, 68\*\* in the respective plate 58\*, 58\*\***.

It also should be noted that FIGS. 6-12 are schematic and do not show the recessed edge portion 59B in the volar side, which is recessed toward the dorsal side of the plate, as is clearly shown in FIG. 3D. However, it is understood that the recessed edge portion 59B, which is shown in FIG. 3D, is present in those embodiments.

It will be obvious to those skilled in the art that modifications may be made to the embodiments described above without departing from the scope of the present invention as defined by the claims.

What is claimed is:

1. A wrist prosthesis, comprising:
    a radial brace defining a proximal end and a distal end, wherein said radial brace includes an articular portion at said distal end, said articular portion defining a first ellipsoidal surface;
    an articular member defining a second ellipsoidal surface, wherein one of said first and second ellipsoidal surfaces is concave and the other is convex, and the convex surface is slidably received in the concave ellipsoidal surface; and
    a carpal plate on said articular member, said carpal plate having top and bottom surfaces defining at least three openings extending through said carpal plate from said top surface to said bottom surface, said openings being non-linearly aligned, wherein each of said three openings is internally threaded and defines a thread-screw axis projecting upwardly from said plate and slanted at an angle between 70 degrees and 85 degrees from a plane defined by the top surface of said carpal plate, and
    at least three screws sized to be threaded into said three openings, each of the screws defining a longitudinal axis such that, when the screws are threaded into the three openings, the longitudinal axes of the three screws diverge from each other, with no two longitudinal axes lying in the same plane, wherein the thread-screw axes are fixed relative to the carpal plate prior to threading any screws into the openings.

2. A wrist prosthesis, comprising:
    a radial brace defining a proximal end and a distal end, wherein said radial brace includes an articular portion at said distal end, said articular portion defining a first ellipsoidal surface;
    an articular member defining a second ellipsoidal surface, wherein one of said first and second ellipsoidal surfaces is concave and the other is convex, and the convex surface is slidably received in the concave ellipsoidal surface; and
    a carpal plate on said articular member, said carpal plate having top and bottom surfaces defining at least three openings extending through said carpal plate from said top surface to said bottom surface, said openings being non-linearly aligned, wherein each of said openings is internally threaded and defines a thread-screw axis fixed relative to the carpal plate, projecting upwardly from said plate and slanted at an angle between 70 degrees and 85 degrees from a plane defined by the top surface of said carpal plate;
    at least three screws sized to be threaded into said three openings, each of said screws defining a longitudinal axis, such that, when the screws are threaded into the three openings, the longitudinal axes of the three screws diverge from each other, with no two longitudinal axes lying in the same plane; and wherein said carpal plate has an outer edge defining a volar side and a dorsal side and a central recess in its volar side which is concave inwardly toward the dorsal side.

3. A wrist prosthesis as recited in claim 2, wherein said first ellipsoidal surface has a distal edge, having a volar side, dorsal side, radial side, and ulnar side, wherein the volar side of said distal edge defines a centrally recessed guide surface aligned with the central recess in the carpal plate.

4. A wrist prosthesis as recited in claim 3, wherein the first ellipsoidal surface is concave, the second ellipsoidal surface is convex, and the second ellipsoidal surface defines a centrally recessed guide surface which is aligned with and extends to the central recess in the carpal plate and which also extends to the centrally recessed guide surface of the first ellipsoidal surface when the second ellipsoidal surface is received in the first ellipsoidal surface.

5. A wrist prosthesis as recited in claim 4, and further comprising:
    an ulnar brace including a rod defining a longitudinal axis, and a ball slidably mounted on said rod for translation along said longitudinal axis relative to said rod;
    wherein said radial brace includes a base at said distal end and a base cover releasably mounted to said base, wherein said base and said base cover define a substantially spherical cavity which receives and rotationally supports said ball.

6. A wrist prosthesis, comprising:
    an ulnar brace including a rod defining a longitudinal axis, and a ball slidably mounted on said rod for translation along said longitudinal axis relative to said rod;
    a radial brace defining a proximal end and a distal end, including a base at said distal end and a base cover releasably mounted to said base, wherein said base and said base cover define a substantially spherical cavity which receives and rotationally supports said ball; and wherein said radial brace further includes an articular portion at said distal end, said articular portion defining a first ellipsoidal surface;
    an articular member defining a second ellipsoidal surface, wherein one of said first and second ellipsoidal surfaces is concave and the other is convex, and the convex surface is slidably received in the concave ellipsoidal surface; and
    a carpal plate on said articular member, said carpal plate having top and bottom surfaces defining at least three openings extending through said carpal plate from said top surface to said bottom surface, said openings being non-linearly aligned, wherein each of said three openings is internally threaded and defines a thread-screw axis projecting upwardly from said plate and slanted at an angle between 70 degrees and 85 degrees from a plane defined by the top surface of said carpal plate; and wherein said three thread-screw axes are fixed relative to the carpal plate prior to inserting a screw into the openings, with the three thread-screw axes diverging from each other, and with no two of the three thread-screw axes lying in the same plane.

7. A wrist prosthesis as recited in claim 6, and further comprising a plurality of screws, each of said screws being received in a respective one of said openings in said carpal plate, wherein each of said screws includes a head portion and a shank, and defines a hollow cavity extending longitudinally through said head portion and through at least a portion of said shank, wherein said shank defines external threads and defines a plurality of through openings extending from said external threads to said hollow cavity.

8. A wrist prosthesis as recited in claim 7, wherein the head portion of each screw also defines external threads, and the threads on the head of each respective screw are engaged with the threads in the respective one of said openings that receives that respective screw.

9. A wrist prosthesis as recited in claim 8, wherein each of the screws has a longitudinal axis which is collinear with the thread-screw axis of the opening in the carpal plate in which the respective screw is received, and the longitudinal axes of at least three screws received in respective openings in the carpal plate diverge from each other, with no two longitudinal axes lying in the same plane.

10. A wrist prosthesis as recited in claim 9, wherein said spherical cavity defines a center and said first ellipsoidal surface extends in the direction of said ulnar brace to a point beyond the center of said spherical cavity.

11. A wrist prosthesis as recited in claim 10, wherein it is known that the human radius bone has an outer surface shape, including the shape of a surface portion of the radius bone that faces the ulna bone; wherein said radial brace member includes an elongated portion which extends toward the proximal end from said base and defines a radius abutment surface that has a shape that conforms to the shape of the surface portion of the human radius bone that faces the ulna bone, said elongated portion defining a plurality of through holes.

12. A wrist prosthesis as recited in claim 6, wherein said base and said first ellipsoidal surface are fixed to each other, said spherical cavity defines a center and said first ellipsoidal surface extends in the direction of the ulnar brace to a point beyond the center of said spherical cavity.

13. A wrist prosthesis as recited in claim 12, wherein the human radius bone is known to have an outer surface shape, including the shape of a surface portion of the radius bone that faces the ulna bone; wherein said radial brace member includes an elongated portion which extends toward the proximal end from said base and defines a radius abutment surface that has a shape that conforms to the shape of the surface portion of the human radius bone that faces the ulna bone, said elongated portion defining a plurality of through holes.

14. A wrist prosthesis as recited in claim 6, and further comprising three screws, each of said screws being received in a respective one of said openings in said carpal plate, wherein each of said screws includes a head portion and a shank, wherein the head portion of each of said screws defines external threads which are threaded into a respective one of said internally threaded openings in said carpal plate.

15. A wrist prosthesis as recited in claim 14, wherein the shank of at least one of said screws is threaded.

16. A wrist prosthesis, comprising:
an ulnar brace including a rod defining a longitudinal axis, and a ball slidably mounted on said rod for translation along said longitudinal axis relative to said rod;
a radial brace defining a proximal end and a distal end, including a base at said distal end and a base cover releasably mounted to said base, wherein said base and said base cover define a substantially spherical cavity which receives and rotationally supports said ball; and wherein said radial brace further includes an articular portion at said distal end, said articular portion defining a first ellipsoidal surface;
an articular member defining a second ellipsoidal surface, wherein one of said first and second ellipsoidal surfaces is concave and the other is convex, and the convex surface is slidably received in the concave ellipsoidal surface;
a carpal plate on said articular member, said carpal plate having top and bottom surfaces defining at least three openings extending through said carpal plate from said top surface to said bottom surface, said openings being non-linearly aligned, wherein each of said openings is internally threaded and defines a thread-screw axis projecting upwardly from said plate and slanted at an angle between 70 degrees and 85 degrees from a plane defined by the top surface of said carpal plate;
a plurality of screws, each of said screws being received in a respective one of said openings in said carpal plate, wherein each of said screws includes a head portion and a shank, and defines a hollow cavity extending longitudinally through said head portion and through at least a portion of said shank, wherein said shank defines an external surface and defines a plurality of through openings extending from said external surface to said hollow cavity;
wherein the head portion of each screw defines external threads, and the threads on the head of each respective screw are engaged with the threads in the respective one of said openings that receives that respective screw;
wherein each of said screws defines a longitudinal axis, and the longitudinal axes of at least three screws received in respective openings in the carpal plate diverge from each other, with no two longitudinal axes lying in the same plane; and
wherein said carpal plate has an outer edge defining a volar side and a dorsal side and a central recess in its volar side which is concave inwardly toward the dorsal side.

* * * * *